United States Patent
Jasperson et al.

(10) Patent No.: US 10,342,411 B2
(45) Date of Patent: *Jul. 9, 2019

(54) HANDLE REMOTE CONTROL FOR USE WITH BRONCHOSCOPY NAVIGATION SYSTEM

(71) Applicant: COVIDIEN LP, Mansfield, MA (US)

(72) Inventors: Keith E. Jasperson, Andover, MN (US); Andrew E. Brown, St. Paul, MN (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/984,619

(22) Filed: May 21, 2018

(65) Prior Publication Data

US 2018/0263465 A1    Sep. 20, 2018

Related U.S. Application Data

(63) Continuation of application No. 14/541,240, filed on Nov. 14, 2014, now Pat. No. 9,974,427.

(51) Int. Cl.
| | |
|---|---|
| *A61B 1/00* | (2006.01) |
| *A61B 1/267* | (2006.01) |
| *A61B 5/06* | (2006.01) |
| *A61B 10/04* | (2006.01) |
| *A61B 1/018* | (2006.01) |

(Continued)

(52) U.S. Cl.
CPC ...... *A61B 1/00066* (2013.01); *A61B 1/00009* (2013.01); *A61B 1/00016* (2013.01);
(Continued)

(58) Field of Classification Search
CPC . A61B 10/04; A61B 1/00009; A61B 1/00016; A61B 1/00039; A61B 1/00045;
(Continued)

(56) References Cited

U.S. PATENT DOCUMENTS

| | | |
|---|---|---|
| 8,357,193 B2 | 1/2013 | Phan et al. |
| 8,968,312 B2 | 3/2015 | Marczyk et al. |

(Continued)

FOREIGN PATENT DOCUMENTS

| | | |
|---|---|---|
| EP | 2594211 A1 | 5/2013 |
| JP | H0815614 A | 1/1996 |

(Continued)

OTHER PUBLICATIONS

U.S. Appl. No. 62/020,240, filed Jul. 2, 2014, inventor: Brown et al.

(Continued)

*Primary Examiner* — Michael T Rozanski

(57) ABSTRACT

A surgical system includes an extended working channel, a magnetic field generator, a sensor, a workstation, a computer readable recording medium, and a remote control handle. The extended working channel is sized for insertion into the working channel of a bronchoscope and to receive one or more instruments therethrough. The sensor is associated with a distal end of the extended working channel for detecting a magnetic field generated by the magnetic field generator. The workstation includes a display and is operably connected to the sensor. The computer readable recording medium is associated with the workstation for storing a software program that enables association of the sensed magnetic field with a location of the sensor and that generates one or more images including one or more fields for presentation on the display. The remote control handle enables manipulation of the one or more fields generated by the software.

19 Claims, 4 Drawing Sheets

(51) Int. Cl.
*A61B 34/20* (2016.01)
*A61B 34/00* (2016.01)
*A61B 17/00* (2006.01)

(52) U.S. Cl.
CPC ...... *A61B 1/00039* (2013.01); *A61B 1/00045* (2013.01); *A61B 1/018* (2013.01); *A61B 1/2676* (2013.01); *A61B 5/062* (2013.01); *A61B 10/04* (2013.01); *A61B 34/20* (2016.02); *A61B 1/0005* (2013.01); *A61B 34/25* (2016.02); *A61B 2017/0046* (2013.01); *A61B 2034/2051* (2016.02); *A61B 2034/742* (2016.02); *A61B 2560/0487* (2013.01)

(58) Field of Classification Search
CPC ... A61B 1/0005; A61B 1/00066; A61B 1/018; A61B 1/2676; A61B 2017/0046; A61B 2034/2051; A61B 2034/742; A61B 2560/0487; A61B 34/20; A61B 34/25; A61B 5/062
See application file for complete search history.

(56) References Cited

U.S. PATENT DOCUMENTS

| 9,974,427 | B2 | 5/2018 | Jasperson et al. |
| 2004/0133075 | A1 | 7/2004 | Motoki et al. |
| 2006/0293556 | A1 | 12/2006 | Garner |
| 2007/0038023 | A1 | 2/2007 | Uchimura et al. |
| 2007/0276180 | A1 | 11/2007 | Greenburg et al. |
| 2008/0015412 | A1 | 1/2008 | Hori |
| 2012/0238806 | A1 | 9/2012 | Mangiardi et al. |
| 2012/0253119 | A1 | 10/2012 | Meloul |
| 2012/0289772 | A1 | 11/2012 | O'Connell et al. |
| 2013/0030249 | A1 | 1/2013 | Vazales et al. |
| 2014/0046174 | A1 | 2/2014 | Ladtkow et al. |
| 2014/0281961 | A1 | 9/2014 | Baker |
| 2014/0316433 | A1 | 10/2014 | Navve et al. |

FOREIGN PATENT DOCUMENTS

| JP | 2003140055 A | 5/2003 |
| WO | 0167035 A1 | 9/2001 |

OTHER PUBLICATIONS

U.S. Appl. No. 62/020,220, filed Jul. 2, 2014, inventor: Brown et al.
International Search Report dated Dec. 11, 2014, issued in PCT/US2014/054511.
European Search Report dated Mar. 15, 2016, issued in European Application No. 15194012.
European Office Action dated Aug. 22, 2018 issued in EP Application No. 15 194 012.

HANDLE REMOTE CONTROL FOR USE WITH BRONCHOSCOPY NAVIGATION SYSTEM

CROSS-REFERENCE TO RELATED APPLICATION

This application is a continuation of U.S. patent application Ser. No. 14/541,240, filed Nov. 14, 2014, now U.S. Pat. No. 9,974,427, the entire contents of which are hereby incorporated by reference.

BACKGROUND

1. Technical Field

The present disclosure relates to surgical instruments and, more specifically, to remote controls for bronchoscopy navigation systems.

2. Discussion of Related Art

A common interventional procedure in the field of pulmonary medicine is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's distal tip; and a lumen or working channel through which instruments may be inserted, including but not limited to placement (e.g., guide wires), diagnostic (e.g., biopsy tools) and therapeutic (e.g., treatment catheters or laser, cryogenic, radio frequency, or microwave tissue treatment probes) instruments. The distal tip of a bronchoscope is steerable. Rotating a lever placed at the handle of the bronchoscope actuates a steering mechanism that deflects the tip in one or more directions.

Bronchoscopies are performed by pulmonologists, also known as bronchoscopists, and are used routinely in the diagnosis and treatment of conditions such as lung cancer, airway stenosis, and emphysema. Bronchoscopies are typically performed by a staff of at least two persons: the bronchoscopist and at least one assistant, usually a nurse. During a typical procedure, the bronchoscopist holds the bronchoscope handle with one hand and the bronchoscope tube with the other hand. The bronchoscopist guides the distal tip of the bronchoscope and/or other instruments by manipulating a proximal end of the bronchoscope tube or the other instruments.

During insertion and operation of the instruments, images from the bronchoscope and/or other instruments may be viewed by the bronchoscopist on display devices. The settings of the display devices and/or the images on the display devices may be manipulated by user interfaces of the display devices. To operate the user interfaces the clinician must remove one hand from the bronchoscope or have an assistant manipulate the user interface. However, the bronchoscope needs to be held steady during insertion and manipulation. Two hands are typically needed to hold the bronchoscope steady.

These difficulties are exacerbated when tools are passed through the working channel of the bronchoscope. For example, when inserting biopsy tools or using the navigation systems such as the EDGE™ and SUPERDIMENSION™ navigation catheters currently sold by Covidien LP. Indeed these additional tools require one hand just for their manipulation. Accordingly, manipulation of a bronchoscope and such an additional tool requires a second person, particularly to simultaneously manipulate the user interface.

Performing a procedure that requires two people is generally more expensive and the potential for error is increased. Hence, it is desirable to modify a procedure so that it may be performed with one or two hands, if possible.

SUMMARY

In an aspect of the present disclosure, a surgical system includes an extended working channel, a magnetic field generator, a sensor, a workstation, a computer readable recording medium, and a remote control handle. The extended working channel is sized for insertion into the working channel of a bronchoscope and to receive one or more instruments therethrough. The sensor is associated with a distal end of the extended working channel for detecting a magnetic field generated by the magnetic field generator. The workstation includes a display and is operably connected to the sensor. The computer readable recording medium is associated with the workstation for storing a software program that enables association of the sensed magnetic field with a location of the sensor and that generates one or more images including one or more fields for presentation on the display. The remote control handle enables manipulation of the one or more fields generated by the software and presented on the display. The one or more instruments may include a locatable guide that houses the sensor.

In aspects, the remote control handle includes a plurality of direction buttons to navigate between the one or more fields presented on the display by the software. The remote control handle may include a selection control button enabling selection of one or more options presented in the one or more fields on the display by the software.

In some aspects, the remote control handle includes a joystick to navigate between the one or more fields presented on the display by the software. The joystick may be vertically depressible to enable selection of one or more options presented in the one or more fields on the display by the software. The system may include a hand selection switch enabling left or right handed operation orienting movements of the software with the selection. The hand selection switch may be disposed on the remote control handle.

In certain aspects, the remote control handle includes a trackball to navigate between the one or more fields presented on the display by the software. The trackball may be vertically depressible to enable selection of one or more options presented in the one or more fields on the display by the software. The remote control handle may include indicia of location on the trackball.

In particular aspects, the remote control handle is in communication with the workstation. The communication may be wireless communication.

In certain aspects, the remote control handle is formed at a proximal end of a locatable guide housing the sensor which is insertable into the extended working channel. The proximal portion of the extended working channel may include a handle for receiving the remote control handle. The remote control handle and the handle of the extended working channel can be secured together to fix the relationship of the extended working channel to the locatable guide. A portion of the handle of the extended working channel is telescopic to enable the fixed locatable guide and the extended working channel to be advanced in unison.

In aspects, the images are images of lungs of a patient. The software may display a 3D model generated from the one or more images. The software may generate a pathway to a target and the location of the sensor on that pathway on the one or more images or 3D model for presentation on the display. The software may enable the presentation of video images from a bronchoscope.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Devices, systems, and methods for navigating to a target within a luminal network, for example, a patient's lungs, are provided in accordance with the present disclosure and described in detail below. The disclosed devices, systems, and methods provide a clinician with easy to use workflow systems guiding the clinician through the various steps involved in performing navigation to a target in the luminal network and improved means of manipulating the workflow or user interface.

These detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure. While the following embodiments are described in terms of luminal navigation of a patient's airways, those skilled in the art will realize that the same or similar devices, systems, and methods may be used in other luminal networks, such as, for example, the vascular, lymphatic, and/or gastrointestinal networks as well.

Figure 1:
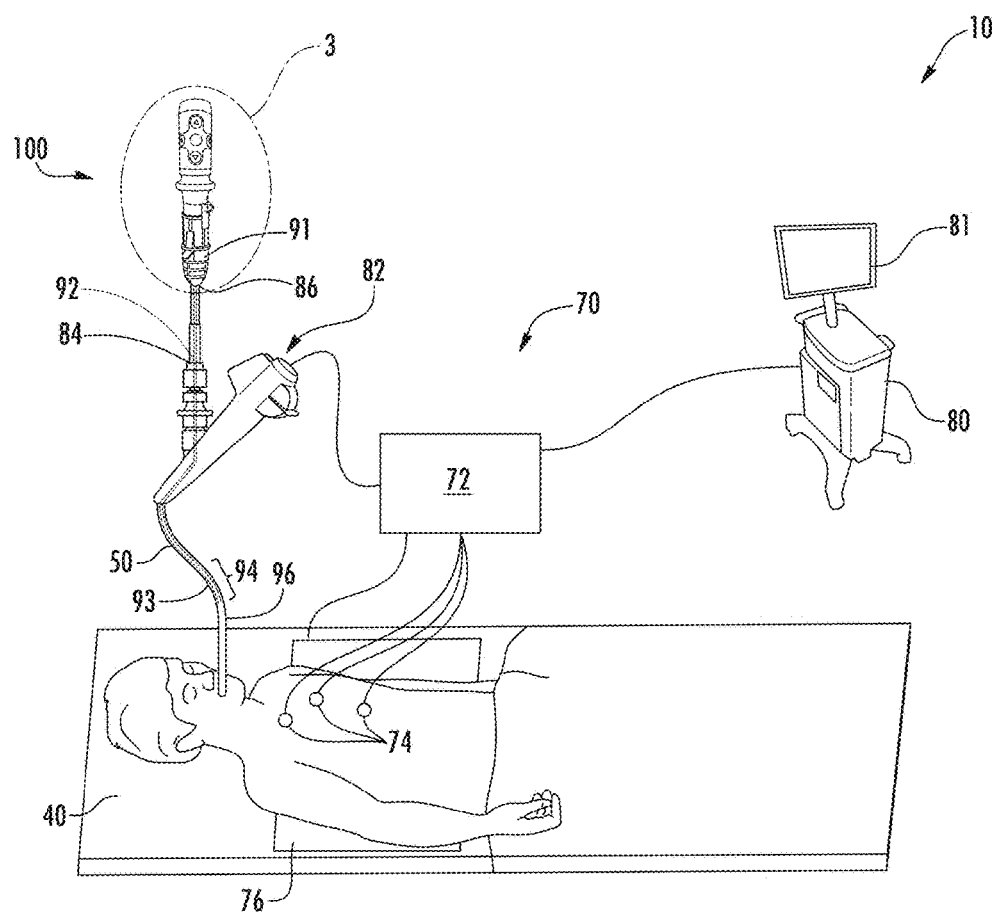
FIG. 1 is a perspective view of an illustrative embodiment of an electromagnetic navigation system in accordance with the present disclosure.

With reference to FIG. 1, an electromagnetic navigation (EMN) system 10 is provided in accordance with the present disclosure. One such EMN system is the ELECTROMAGNETIC NAVIGATION BRONCHOSCOPY® system currently sold by Covidien LP. Among other tasks that may be performed using the EMN system 10 are planning a pathway to target tissue, navigating a catheter guide assembly to the target tissue, deploying a biopsy tool through the catheter assembly into the target tissue to obtain a tissue sample from the target tissue using the biopsy tool, digitally marking the location where the tissue sample was obtained in a data file related to the planned pathway, and placing one or more echogenic markers at or around the target.

Figure 2:
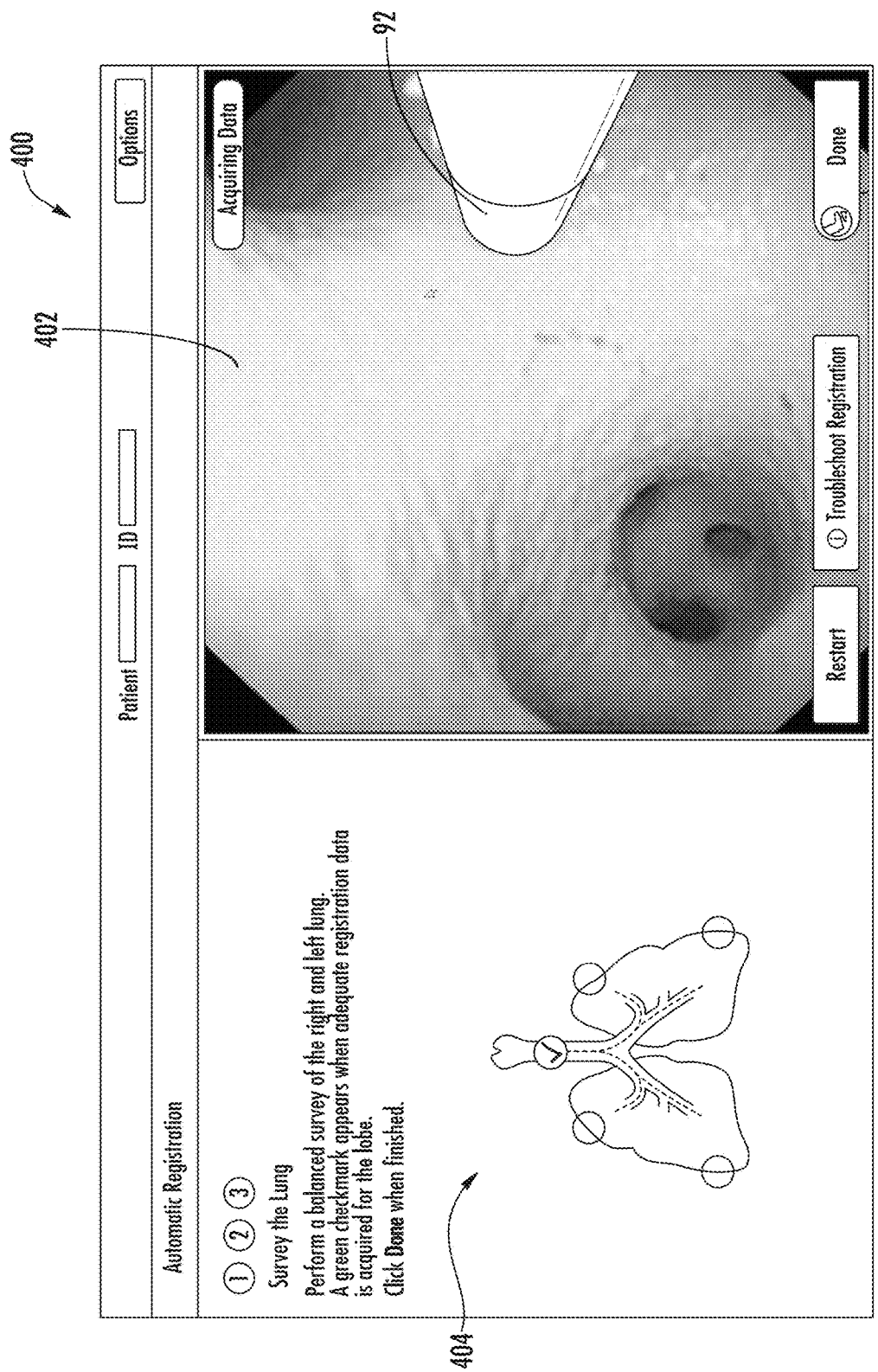
FIG. 2 is an illustration of a user interface of the workstation of FIG. 1 presenting a view for performing registration in accordance with the present disclosure.

EMN system 10 generally includes an operating table 40 configured to support a patient; a bronchoscope 50 configured for insertion through the patient's mouth and/or nose into the patient's airways; a tracking system 70 including a tracking module 72, a plurality of reference sensors 74, and an electromagnetic field generator 76; a workstation 80 including software and/or hardware used to facilitate pathway planning, identification of target tissue, navigation to target tissue, and digitally marking the biopsy location FIG. 1 also depicts a catheter guide assembly 100 usable with the EMN system 10. The catheter guide assembly 100 includes a handle 91, which is connected to an extended working channel (EWC) 96. The EWC 96 is sized for placement into the working channel of a bronchoscope 50. In operation, a locatable guide (LG) 92, including an electromagnetic (EM) sensor 94, is inserted into the EWC 96 and locked into position such that the sensor 94 extends a desired distance beyond the distal tip 93 of the EWC 96. As shown in FIG. 2, the LG 92 is not quite to the desired location extending beyond the distal end of the EWC 96. The location of the EM sensor 94, and thus the distal end of the EWC 96, within an electromagnetic field generated by the electromagnetic field generator 76 can be derived by the tracking module 72, and the workstation 80. The catheter guide assembly 100 has a handle 91 that can be manipulated by rotation and compression to steer the distal tip 93 of the LG 92 and the extended working channel 96. An example of a suitable catheter guide assembly is currently marketed and sold by Covidien LP under the name EDGE™ Procedure Kits. For a more detailed description of the catheter guide assembly 100 reference is made to commonly-owned U.S. Provisional Patent Application Ser. No. 62/020,240 filed on Jul. 2, 2014 and entitled System and Method for Navigating within the Lung, the entire contents of which are hereby incorporated by reference.

As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment, e.g., a display 81, for displaying the video images received from the video imaging system of bronchoscope 50. As shown, the display 81 is integrated with and is also the display for workstation 80; however, it is contemplated that the display could also be a separate monitor (not shown).

The catheter guide assembly 100 including LG 92 and EWC 96 are configured for insertion through a port 84 formed at the proximal end of bronchoscope 50 into the patient's airways (although the catheter guide assembly 100 may alternatively be used without bronchoscope 50). The LG 92 and EWC 96 are selectively lockable relative to one another via a locking mechanism (not shown). A six degrees-of-freedom electromagnetic tracking system 70, e.g., similar to those disclosed in U.S. Pat. No. 6,188,355 entitled Wireless Six-degree-of-freedom Locator, and published PCT Application No. WO 01/67035 entitled Object Tracking using a Single Sensor or a Pair of Sensors, the entire contents of each of which are incorporated herein by reference, or any other suitable positioning measuring system, is utilized for performing navigation, although other configurations are also contemplated. Tracking system 70 is configured for use with catheter guide assembly 100 to track the position of the EM sensor 94 as it moves in conjunction with the LG 92 and EWC 96 through the airways of the patient, as detailed below.

During procedure planning, workstation 80 utilizes computed tomographic (CT) image data for generating and viewing a three-dimensional model ("3D model") of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display 81 associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure. An example of a suitable pathway planning system and method is described in U.S. patent application Ser. No. 13/838,805 entitled Pathway Planning System and Method, filed on Mar. 15, 2014, the entire contents of each of which are incorporated herein by reference.

During navigation, EM sensor 94, in conjunction with tracking system 70, enables tracking of EM sensor 94 as EM sensor 94 is advanced through the patient's airways. As shown in FIG. 2, view 400 of monitor 81 presents a clinician with a video feed 402 from bronchoscope 50 and a lung survey 404 from the planning phase. The lung survey view 400 is one of a variety of screens available to a user when utilizing an EMN navigation software such as that described U.S. Provisional Patent Application Ser. No. 62/020,240, incorporated herein above. Video feed 402 from bronchoscope 50 provides the clinician with a real-time video of the interior of the patient's airways at the distal end of bronchoscope 50. Video feed 402 allows the clinician to visually navigate the bronchoscope 50 through the airways of the lungs of the patient. The clinician advances the bronchoscope 50 with the EWC 96 and the LG 92 extending therefrom through the airways of the lungs until the real-time position of the airways of the lungs of the patient are registered with the pathway planned during the planning phase. More details regarding the process of registration are set forth in U.S. Patent Application No. 62/020,220 filed Jul. 2, 2014 and entitled REAL-TIME AUTOMATIC REGISTRATION FEEDBACK, the entire contents of which are incorporated herein by reference.

FIG. 2 provides a specific example of one view in a pathway navigation and procedure software. In this view as well as many others provided in such a software package, before and during the registration process as well as during the navigation and treatment phases of such systems, the clinician may be required to select tabs on the monitor 81 to select a target, change tabs, select a navigation plan, activate a navigation plan, manipulate an image (e.g., zoom in and out, or rotate), or provide indicia to the workstation 80 (e.g., "click" a dialog box or choose an option). As described above, removal of a clinician's hands from the bronchoscope 50 or the catheter guide assembly 100 is required for operation of such software and making selections, for example on a display 81 or necessitates the use of another clinician to fully operate the system.

Figure 3:
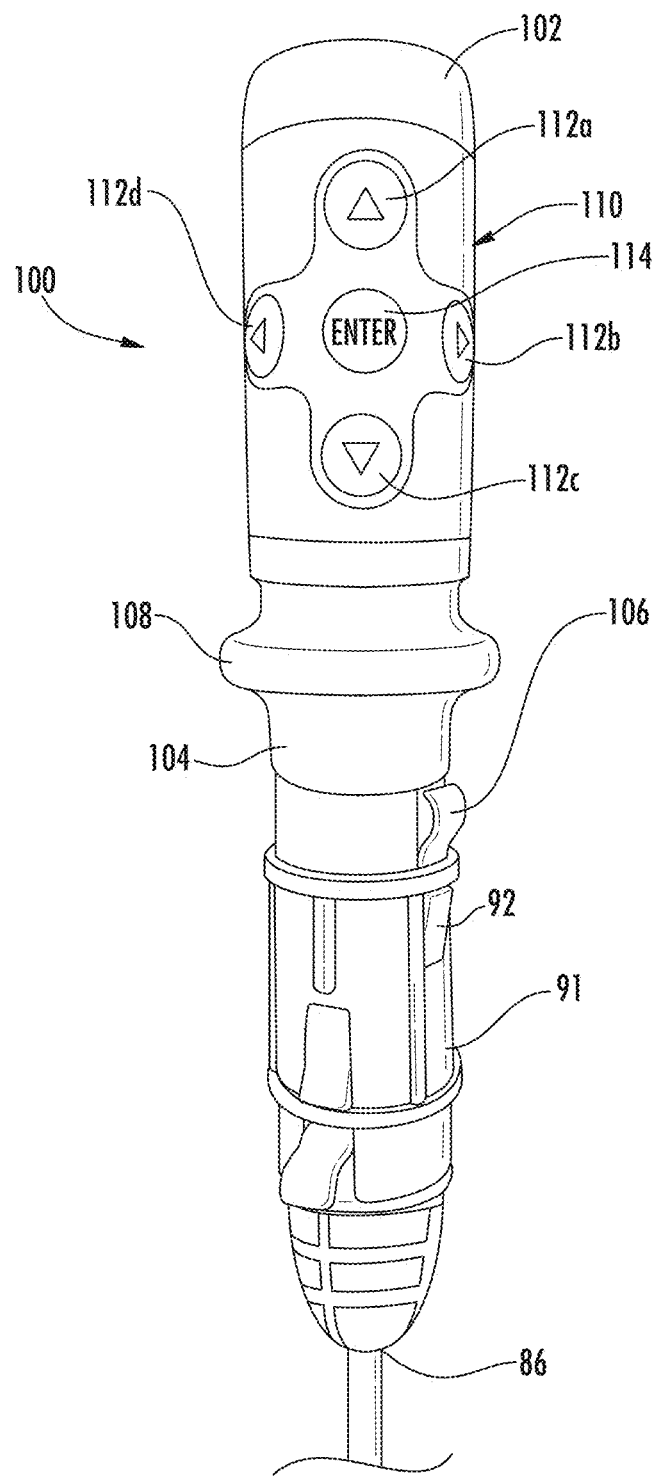
FIG. 3 is an enlarged view of the indicated area of detail of FIG. 1.

Referring to FIGS. 1 and 3, the EMN system 10 includes a handle remote 102 that may form the proximal end of the LG 92, and is releasably coupled to a handle 91 which forms the proximal end of the EWC 96. The handle 91 is connected at its distal end to port 84 to the working channel of the bronchoscope 50. The handle 91 includes a telescopic portion 86, enabling the LG 92 and EWC 96 to move together through the working channel of bronchoscope 50. The handle remote 102 is in communication with the workstation 80 to allow a clinician to interface with the workstation 80 without releasing the handle remote 102 or the bronchoscope 50. The handle remote 102 may be wired to the workstation 80 or be in wireless communication with the workstation 80. The wireless connection may be via radio frequency, optical, WIFI, Bluetooth® (an open wireless protocol for exchanging data over short distances (using short length radio waves) from fixed and mobile devices, creating personal area networks (PANs)), ZigBee® (a specification for a suite of high level communication protocols using small, low-power digital radios based on the IEEE 802.15.4-2003 standard for wireless personal area networks (WPANs)), etc.

The handle remote 100 includes a proximal end 101 and a distal end 104 having a securement device 106. The distal end 104 of the handle remote 100 is sized and dimensioned to be received within and releasably couple to the proximal end of the handle 91. The securement device 106 may be a clip that is received within a slot 97 defined in handle 91 which rotationally fix the securement device 106 to the handle 91. Alternatively, the securement device 106 may releasably couple the handle remote 100 to the handle 91 while allowing the handle remote 100 to rotate relative to the handle 91.

With particular reference to FIG. 3, the handle remote 100 includes a remote interface 110 having directional controls 112a-d and a selection control 114. The direction controls 112a-112d allow a clinician to move a cursor on the display 81 of the workstation 80 in a manner similar to an input device such as a computer mouse (e.g., to move objects selected about the monitor 81, to select dialog boxes or buttons on monitor 81). Each of the directional controls 112a-d are orientated to the display 81 of the workstation 80 (i.e., directional control 112a is up on the display 81, direction control 112b is right on the display 81, etc.). The selection control 114 allows a clinician to choose options on the monitor 81 (e.g., activate a dialog box, select a plan, or mark a point on the display 81). The selection control 114 may perform operations on the display 81 similar to operations performed by a left mouse click. It is contemplated that the remote interface 110 may include an option control (not shown) that performs operations on the display 81 similar to operations performed by a right mouse click.

The remote interface 110 may be sized and configured to be gripped by the hand of a clinician during manipulation of the handle 102. The handle remote 102 may include a distal ring 108 proximal to the securement device 106 to that may prevent accidental disengagement of a hand of a clinician from the handle remote 102 (e.g., the hand of a clinician sliding off of the handle remote 102). In addition, the distal ring 108 provides tactile indicia to a clinician to the position of the distal end 104 of the handle remote 102 to permit the clinician to position the handle remote within a hand.

Figure 4:
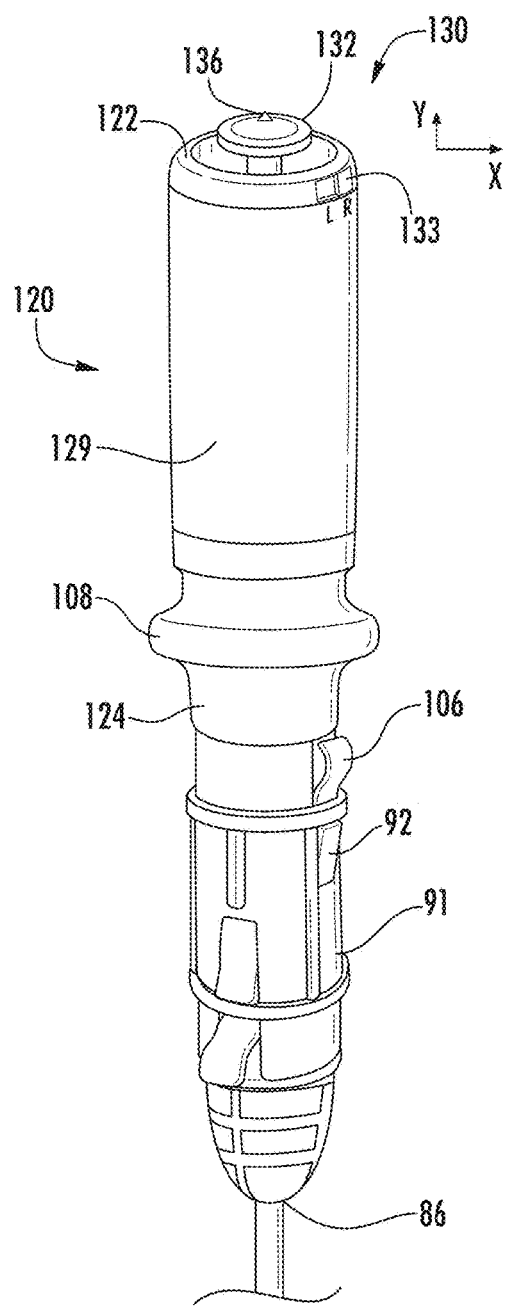
FIG. 4 is another embodiment of a handle remote in accordance with the present disclosure.

With reference to FIG. 4, another handle remote 120 includes proximal end 122 and a distal end 124. Similar to the distal end 104 of the handle remote 100, the distal end 124 of the handle remote 120 includes a securement device 106 for securing the handle remote 120 to the handle 91. The handle remote 120 includes a body 129 and a user interface 130. The body 129 is sized and configured to be gripped by the hand of a clinician during manipulation of the handle 91. The body 129 includes a distal ring 108.

The remote interface 130 is disposed on the proximal end 122 of the handle remote 120 and includes a directional control 132 that allows a clinician to move a cursor on the display 81 of the workstation 80 in a similar manner to the direction controls 112a-d of the remote interface 110 detailed above. The direction control 132 is joystick that is configured to be engaged by a thumb of a clinician. The direction control 132 may be moveable in any direction or may be limited to movement in just the X and Y axis (FIG. 4). The directional control 132 may include indicia 136 to a clinician to facilitate orientation of the X axis of the directional control 132 with right and left movement of the cursor on the display 81 and to orient the Y axis of the directional control 132 with up and down movement on the display 81. The indicia 136 may provide a tactile surface such that a clinician may orientate the direction control 132 without diverting attention away from the surgical procedure. The direction control 132 may be depressible to choose options on the display 81 similar to the selection control 114 of the remote interface 110 detailed above. The direction control 132 may provide tactile and/or haptic feedback to the clinician when the direction control 132 is depressed.

In embodiments, the body 129 may orientate the handle remote 120 in a hand of a clinician such that the X and Y axis of the direction control 132 are orientated with movement of a thumb of the hand of the clinician (e.g., when the hand grips the body 129 of the handle remote 120, movement of the direction control 132 to the right moves the cursor to the right). It will be appreciated that in such embodiments, the handle remote 120 may be right handed or left handed. In some embodiments, the remote interface 130 may include an orientation switch 133 to choose between right and left handed operation of the remote handle 120.

Figure 5:
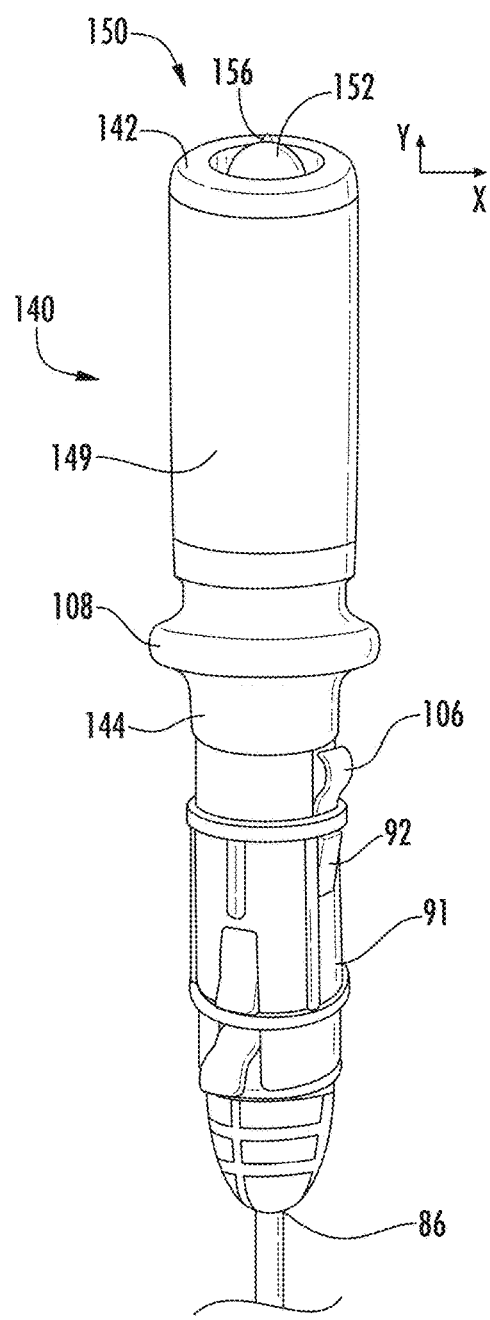
FIG. 5 is yet another embodiment of a handle remote in accordance with the present disclosure.

With reference to FIG. 5, another handle remote 140 includes a proximal end 142 and a distal end 144. Similar to the distal end 104 of the handle remote 100, the distal end 144 of the handle remote 140 includes a securement device 106 for securing the handle remote 140 to the handle 91. The handle remote 140 includes a body 149 and a remote interface 150. The body 149 of the handle remote 140 is similar to the body 129 of the handle remote 120 detailed above.

The remote interface 150 includes a direction control 152 in the form of a trackball. The direction control 152 is operable in a similar manner to the direction control 132 of remote interface 130. The direction control 152 may be depressible to choose options on the display 81 similar to the direction control 132 detailed above. The remote interface 150 may include an indicia 156 to provide a tactile surface such that a clinician may orientate the direction control 152 without diverting attention away from a surgical procedure in a similar manner to indicia 136 detailed above. The indicia 156 may be disposed on the proximal end 142 of the handle remote 140.

While several types of remote interfaces (e.g. remote interfaces 110, 130, 150) are shown herein, it is contemplated that the remote interface may also be an optical sensor to detect movement of a finger of a clinician over the sensor, a track pad, or a touch screen. It is also contemplated that the remote interface may receive voice commands from a clinician to operate the workstation 80.

By providing a handle remote (e.g., handle remote 100, 120, 140) a clinician may manipulate the handle 91 to guide the LG 92 and EWC 96 to a target within a lung of a patient and operate the workstation 80 without releasing the handle 91 or the bronchoscope 50. By allowing manipulation of the handle 91 and the workstation 80 with one hand of a clinician, the clinician can operate the workstation 80 and the handle 91 without drawing the clinician's attention away from the monitor 81 of the workstation 80. In addition, the number of clinicians for a given procedure may be reduced, which in turn reduces the cost of the procedure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical system comprising:
    an extended working channel sized for insertion into a working channel of a bronchoscope;
    a proximal handle secured about a proximal portion of the extended working channel and configured to selectively receive an instrument therethrough; and
    a remote control handle configured to interact with a GUI on a display and having a distal portion releasably coupled directly to the proximal handle of the extended working channel.

2. The surgical system according to claim 1, further comprising a magnetic field generator configured to generate a magnetic field.

3. The surgical system according to claim 1, wherein the remote control handle includes a plurality of directional buttons, the plurality of directional buttons configured to navigate between fields on the display.

4. The surgical system according to claim 1, wherein the remote control handle includes a selection control button configured to select one or more options on the display.

5. The surgical system according to claim 1, wherein the remote control handle includes a joystick configured to navigate between one or more fields on the display.

6. The surgical system according to claim 5, wherein the joystick is vertically depressible to enable selection of one or more options presented in the one or more fields on the display.

7. The surgical system according to claim 5, further comprising a hand selection switch configured to enable left or right handed operation of the remote control handle.

8. The surgical system according to claim 1, wherein the remote control handle includes a trackball configured to navigate between one or more fields on the display.

9. The surgical system according to claim 8, wherein the trackball is vertically depressible to enable selection of the one or more fields on the display.

10. The surgical system according to claim 9, wherein the remote control handle includes an indicia of location on the trackball.

11. The surgical system according to claim 1, wherein the remote control handle is configured to be in wireless communication with a workstation.

12. The surgical system according to claim 1, wherein the remote control handle and the proximal handle of the extended working channel are configured to be secured together fixing the extended working channel relative to a sensor of a locatable guide inserted through the extended working channel.

13. The surgical system according to claim 1, wherein a portion of the proximal handle of the extended working channel is telescopic which enables a sensor of a locatable guide inserted through the extended working channel and extended working channel to be advanced in unison.

14. The surgical system according to claim 1, further comprising a locatable guide extendable through the extended working channel, the locatable guide having a sensor associated with a distal end of the extended working channel, the sensor configured to locate the distal end of the extended working channel within a magnetic field.

15. A surgical system comprising:
an extended working channel sized for insertion into a working channel of a bronchoscope, the extended working channel configured to allow one or more instruments to selectively pass through the extended working channel from a proximal end thereof to a distal end thereof; and
a remote control handle directly releasably coupled to a proximal portion of the extended working channel, the remote control handle configured to interact with a GUI on a display, the remote control handle having a hand selection switch enabling left or right handed operation of the remote control handle.

16. The surgical system according to claim 15, further comprising a magnetic field generator configured to generate a magnetic field.

17. The surgical system according to claim 15, further comprising a workstation including the display.

18. The surgical system according to claim 15, wherein the remote control handle is movable independent of a locatable guide inserted through the extended working channel.

19. The surgical system according to claim 15, further comprising a surgical instrument received within the extended working channel.

* * * * *